United States Patent [19]

Strehlke et al.

[11] Patent Number: 5,045,558
[45] Date of Patent: Sep. 3, 1991

[54] N-SUBSTITUTED IMIDAZOLES AND THEIR USE IN PHARMACEUTICAL AGENTS

[75] Inventors: Peter Strehlke; Rolf Bohlmann; David Henderson; Yukishige Nishino, all of Berlin, Fed. Rep. of Germany

[73] Assignee: Schering Aktiengesellschaft, Berlin and Bergkamen, Fed. Rep. of Germany

[21] Appl. No.: 331,399

[22] Filed: Mar. 31, 1989

[30] Foreign Application Priority Data

Mar. 31, 1988 [DE] Fed. Rep. of Germany ....... 3811574

[51] Int. Cl.$^5$ ................. C07D 233/60; C07D 233/61; A61R 31/415
[52] U.S. Cl. .................................... 514/399; 514/397; 548/335; 548/336
[58] Field of Search ................ 548/335, 336; 514/397, 514/399

[56] References Cited

U.S. PATENT DOCUMENTS

| 4,226,878 | 10/1980 | Iizuka et al. | 548/335 X |
| 4,405,634 | 9/1983 | Thorogood | 514/396 |
| 4,731,370 | 3/1988 | Watanabe et al. | 514/332 |
| 4,778,817 | 10/1988 | Lau et al. | 514/399 |
| 4,916,144 | 4/1990 | Strehlke | 548/336 |

OTHER PUBLICATIONS

*Chemical Abstracts*, 83:157710t(1975)[K. Baggaley, et al., *J. Med. Chem.* 1975, 18(8), 833-6].
*Chemical Abstracts*, 104:224901y (1986)[G. Wess, et al., Ger. Offen. 3,424,944, 2/6/86].
*Chemical Abstracts*, 108:17777e (1988)[S. Nishimura et al., JPN. Kokai Tokkyo Koho 62, 205,002, 9/9/87].

*Primary Examiner*—Mary C. Lee
*Assistant Examiner*—Lenora Miltenberger
*Attorney, Agent, or Firm*—Millen, White & Zealano

[57] ABSTRACT

The invention relates to N-substituted imidazoles, processes for their production as well as their use in pharmaceutical agents. The compounds according to the invention have aromatase-inhibiting properties.

17 Claims, No Drawings

N-SUBSTITUTED IMIDAZOLES AND THEIR USE IN PHARMACEUTICAL AGENTS

SUMMARY OF THE INVENTION

This invention relates to N-substituted imidazoles, processes for their production as well as their use in pharmaceutical agents.

The new N-substituted imidazoles are characterized by general formula I

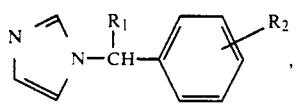

in which $R_1$ is a hydrogen atom, a saturated or unsaturated, straight-chain or branched-chain hydrocarbon radical with 1 to 10 carbon atoms, a cyclic hydrocarbon radical with 3 to 9 carbon atoms, a cycloalkylalkyl radical with 4 to 12 carbon atoms or an arylalkyl radical with 7 to 10 carbon atoms, and $R_2$ is a substituted straight-chain or branched-chain, saturated or unsaturated hydrocarbon radical with 1 to 10 carbon atoms, an optionally derivatized formyl group, an optionally substituted alkanoyl group with 2 to 10 carbon atoms, an optionally substituted benzoyl group or an optionally derivatized carboxyl group.

The compounds can also be present in the form of their salts.

The straight-chain or branched-chain, saturated or unsaturated hydrocarbon radical with 1 to 10 carbon atoms suitable as the radical $R_1$ are, for example, e.g., alkyl, alkenyl, e.g, the methyl, ethyl, propyl, propenyl, isopropyl, butyl, hexyl, octyl and decyl radical. The propyl radical is preferred. The cyclic hydrocarbon radicals include all those with 3 to 9 carbon atoms. Exemplary cycloalkyl radicals, include, e.g., the cyclopentyl and cyclohexyl radical. Cycloalkylalkyl radicals include all those with 4 to 12 carbon atoms, e.g., the cyclopentylmethyl and cyclohexylmethyl radicals. The arylalkyl group includes all those with 7 to 10 carbon atoms, e.g., benzyl.

The substituted straight-chain or branched-chain saturated or unsaturated hydrocarbon radicals with 1 to 10 carbon atoms which are substituted singly or repeatedly (e.g., 1–3) on the chain with substituents which may be the same or different. Suitable as radicals $R_2$ are, for example, substituted methyl, ethyl, propyl, benzyl, phenyl and ethenyl groups. As substituents of these groups there can be mentioned, for example, halogen (fluorine, chlorine, bromine and iodine), alkoxy having 1–6 carbon atoms (e.g., methoxy, butoxy), phenoxy, amine radicals (e.g., $C_{1-4}$-alkyl amino), hydroxyl, cyano, carboxyl containing radicals, carboxylic acid $C_{1-10}$-alkyl esters and carboxylic acid amide radicals, e.g., mono or di-$C_{1-6}$-alkyl amides, anilides or

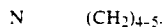

Hydroxyl, cyano, methoxy, butoxy, phenoxy, amino, pyrrolidinyl, carboxyl, carboxylic acid ester and carboxylic acid amide are preferred substituents.

Further, $R_2$ has the meaning of a formyl group which may optionally be derivatized. Suitable derivatives include, e.g., those obtained by the reaction of the formyl group with an amine or an amine derivative. The products, which can be obtained by reaction with, e.g., hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine and aniline, are preferred.

Further, $R_2$ has the meaning of a carboxyl group or derivatives thereof. Carboxylic acid, carboxylic acid, $C_{1-10}$-alkyl esters and carboxylic acid amides (e.g., mono- or di-$C_{1-6}$-alkylamides, anilides or

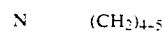

can be mentioned, for example, as suitable derivatives. Methyl, ethyl and butyl ester as well as carboxylic acid amide, carboxylic acid isopropylamide, carboxylic acid anilide and carboxylic acid pyrrolidinylamide are particularly suitable.

Further, $R_2$ can be a substituted or unsubstituted alkanoyl group with 2 to 10 carbon atoms. The alkanoyl group can be straight-chain or branched-chain and be substituted singly or repeatedly (1–3) with the same or different substituents on any position of the chain. Preferred alkanoyl groups are acetyl, propionoyl, butyryl, valeryl and caproyl groups.

Halogen atoms (e.g., fluorine, chlorine, bromine or iodine), ether (e.g., $C_{1-4}$-alkoxy), amino, hydroxyl and cyano groups are suitable as substituents of the alkanoyl group.

$R_2$ can also be substituted or unsubstituted benzoyl group. When substituted, the benzoyl can be substituted 1–3 times, with the same or different substituents in any position(s) on the group. Substituents of the substituted benzoyl group suitable as radical $R_2$ are halogen atoms (fluorine, bromine, iodine and chlorine), $C_{1-4}$-alkyl, methoxy, amino, hydroxyl and cyano groups.

The radical $R_2$ can be on the aromatic substance in the 2, 3 or 4 position.

As possible salts of the compounds of general formula I there can be mentioned physiologically compatible salts of organic or inorganic acids. The malonate, succinate, hydrochloride and hydrobromide are especially suitable as salts.

The compounds of general formula I are inhibitors of estrogen biosynthesis (aromatase inhibitors). Therefore they are suitable for treating diseases which are caused by estrogens or are dependent on estrogens. Thus, they are suitable for treating estrogen-induced or estrogen-stimulated tumors, such as, for example, breast cancer or prostate hyperplasia (The Lancet. 1984, 1237–1239).

The compounds according to the invention are also valuable for affecting fertility. Thus, male infertility, which results from increased estrogen levels, can be eliminated with the new active ingredients. Further, the compounds can be used in women in the reproductive age as a birth control agent to inhibit ovulation by estrogen deprivation.

The aromatase inhibitors are also suitable for treating imminent myocardial infarction, since increased estrogen levels can precede a myocardial infarction in the male (see, e.g., U.S. Pat. No. 4,289,762).

Besides steroids, known substances exhibiting aromatase-inhibiting action are nonsteroidal substances; such as, for example, the various nitrogen heterocycles described in the European patent applications, publication numbers 0165777 to 0165784, the substituted glutaric acid imides described in *J. Med. Chem.*, 1986, 29, pages 1362-1369, the substituted imidazobenzenes described in the European patent application, publication number 0165904 and the substituted heterocyclically substituted toluene nitriles described in the European patent application, publication number 0236940.

The compounds of this application are distinguished from the compounds known so far in that they inhibit the enzyme system of aromatase more strongly and at the same time more selectively. The selective effect is marked in that it adversely affects other enzyme systems to a lesser extent.

Biological tests A and B are used to determine the enzymatic activities and enzyme selectivity of the compounds.

TEST A

Determination of Aromatase Activity

The capabilities of compounds to inhibit the enzyme system of aromatase is tested on microsomes obtained from human placenta. The release of tritium-labeled water ($^3H_2O$), which is released as reaction product in the aromatizing of (1beta-$^3$H) androstrenedione to estrogen, is measured according to the methods of Thompson and Siiteri (*J. Biol. Chem.* Z49, 5364-72 (1974)). The corresponding inhibition values ($K_1$, aromatase) are determined according to the method of Dixon (*Biochem. J.* 94, 760 (1965) by graphic determination of the application of 1/v against the inhibition concentration.

TEST B

Determination of 11-beta Hydroxylase Activity

The 11beta-hydroxylase activity is measured on mitochondria, obtained from bovine suprarenals. The reaction of [1,2-$^3$H]-17alpha-hydroxy-11-deoxycorticosterone in cortisol is determined by thin-film chromatography of the resulting reaction products according to a method of Mitani et al (J. Biol. Chem 250, 8010-15 (1975)). The concentration of the examined compound is determined, in which the reaction is inhibited by 50%, and the substrate concentration corresponds to the apparent $K_m$ value. For example, for the aromatase inhibitors according to the invention, >4-[1-(1-imidazole)-butyl]-phenyl>-pentyl-ketone (compound 2) and 4-[1-(1-imidazolyl)-butyl]-benzoic acid butyl ester (compound 3) in comparison with the aromatase inhibitor known in the literature (compound 1) 4-[1-(1-imidazolyl)-butyl]-benzonitrile (European patent application, publication No. 0 236 940) exhibit more selective effectiveness with simultaneously stronger inhibition actions of aromatase than compound 1.

| Compound | Test A $K_i$ aromatase | Test B IC$_{50}$ 11 beta-hydroxylase |
|---|---|---|
| Compound 1 | 1.1 nmol/L | 94 nmol/L |
| Compound 2 | 0.42 nmol/L | 1.5 micromol/L |
| Compound 3 | 0.87 nmol/L | 750 nmol/L |

The amounts of the compounds to be administered vary within a wide range and can cover any effective amounts. Depending on the condition to be treated and the kind of administration, the amount of compounds administered can be 0.0001-10 mg/kg of body weight, preferably 0.001-1 mg/kg of body weight, per day.

The dosage is 0.0001-10 mg/kg/day, preferably 0.0001-1 mg/kg/day, analogous to the known agent aminoglutethimide when administered to treat estrogen-stimulated tumors, 0.0001-10 mg/kg/day, preferably 0.0001-1 mg/kg/day when administered analogous to the known agent aminoglutethimide to treat male infertility, 0.0001-10 mg/kg/day, preferably 0.0001-1 when administered analogously to the known agent 4-hydroxy-4-androstene-3,17-dione to inhibit ovulation, and 0.001-3 mg/kg/day, preferably 0.01-2 when administered analogously to the known agent 4-hydroxy-4-androstene-3,17-dione for the treatment of imminent myocardial infarction.

For the treatment of estrogen-stimulated tumors, a dosage range of 0.005-0.05 mg/kg/day is mostly preferred.

Capsules, pills, tablets, dragees, etc. are suitable for oral application. Besides the active ingredient, the dosage units can contain a pharmaceutically compatible vehicle, such as, for example, starch, sugar, sorbitol, gelatin, lubricant, silicic acid, talc, etc. The individual dosage units for oral application can contain, for example, 0.05-50 mg of active ingredient (aromatase inhibitor).

For parenteral administration the active ingredients can be dissolved or suspended in a physiologically compatible diluent. Very often oils with or without addition of a solubilizer, a surfactant, a suspension or emulsion mixture are used as diluent. As examples for the oils used there can be mentioned: olive oil, peanut oil, cottonseed oil, soybean oil, castor oil and sesame oil.

The compounds can also be used in the form of a depot injection or an implant preparation, which can be formulated so that a delayed active ingredient release is made possible.

Implants can contain as inert materials, for example, biodegradable polymers or synthetic silicones, such as, for example, silicone rubber. Moreover, the active ingredients can be worked, for example, into plasters for percutaneous application.

Thus the invention also relates to pharmaceutical preparations and the use of the compounds for the production of these preparations for treatment of estrogen-caused diseases.

The invention further relates to processes for the production of substituted imidazoles of general formula I, characterized in that a) compound of general formula II

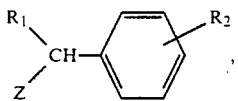 (II)

in which
R₁ and R₂ have the meaning given above, and Z means a leaving group, is reacted with a compound of general formula III

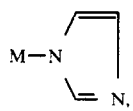 (III)

in which
M means a hydrogen atom or an alkali metal atom, or b) a compound of general formula IV

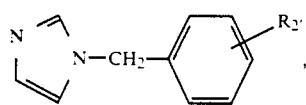 (IV)

in which
R₂' has the same meaning as R₂ in formula I provided that R₂' is an electrophilic, nondeprotonatable radical, is reacted, in the presence of a base, with a compound of general formula V

R₁—Z (V)

in which
R₁ has the meaning mentioned above and
Z means a leaving group, or c) a compound of general formula VI

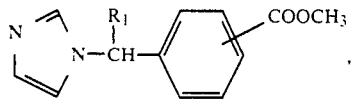 (VI)

in which
R₁ has the meaning mentioned above, and is converted with a reducing agent into the hydroxymethyl compound, which may be reacted with a halogenating agent to form a halomethyl compound, which may be converted with a metal cyanide into the cyanomethyl compound or with a methyl alkoxide into the alkoxymethyl compound or with ammonia into the aminomethyl compound or with an amine into the substituted aminomethyl compound. The compound of general formula VI may be hydrolytically converted into the carboxyl compound or into the carboxylic acid amide or under transesterification conditions with an alcohol into a carboxylic acid ester. When a carboxyl compound is formed, it may optionally be reacted with an alcohol to form the carboxylic acid ester or with a halogenating agent to form the carboxylic acid halide, which carboxylic acid halide may be reacted with ammonia or amines to form carboxylic acid amides. The hydroxymethyl compound may also be reacted with manganese dioxide to form an aldehyde. The aldehyde may be reacted with amines or substituted amines into imines or substituted imines or with Wittig reagents into unsaturated compounds. The unsaturated compounds thus formed may be subjected to hydrogenation conditions to form saturated compounds. The aldehyde may also be reacted with metalorganic compounds to form secondary alcohols which may be reacted with a oxidizing agent to form the substituted alkanoyl derivatives or benzoyl derivatives.

Easily substitutable groups, known from the literature, are suitable as leaving groups Z for the reactions mentioned under a). As such functional groups suitable for leaving group capability can be mentioned, for example, the mesyl, tosyl, triflat and acetyl group. Also the halogens, e.g., chlorine and bromine, are also suitable. The method are described, among others, in Eur. J. Med. Chem. 1979, pages 231-237. Hydrogen and alkali metal atoms, for example, are suitable as substituents M of general formula III. Lithium, sodium and potassium are preferred as alkali metals.

The reactions, which are performed under a), the reactions of compounds of general formula II with compounds of general formula III, can be performed in all inert organic solvents. For example, dimethylformamide, dimethyl sulfoxide and various ethers (e.g., tetrahydrofuran, dioxane and diethyl ether) are suitable as solvents.

The reaction of the compounds of formula II with imidazole (formula III, M=H) can also be performed without a solvent and at temperatures between the melting point and the boiling point of the imidazole, preferably between 100° C. and 200° C.

The production of the compounds of general formula I can also be performed according to process b). In this case, reaction of compounds of general formula IV with compounds of general formula V takes place. All usual leaving groups, e.g., those named in a), are suitable as leaving group Z of the compounds of general formula V.

For the production of the compound of general formula I according to process b) the corresponding benzyl anion is produced with bases from the compounds of general formula IV and reacted by standard methods with the compounds of general formula V. The benzyl—CH₂— group in the compounds of general formula IV, which must contain electrophilic, even nondeprotonatable radicals R₂, can be deprotonated with bases, e.g., by reaction with tertiary amines, sodium hydride, lithium hydride or lithium diisopropylamide and reacted with compounds of general formula V.

The reaction may be carried out with or without a solvent at a temperature of −100° to +100° C. When a solvent is used, suitable solvents include inert solvents, such as ethers, e.g., tetrahydrofuran, dioxane and diethylether or dimethylforamide, etc.

The compounds of general formula I according to the invention can also be produced according to process c). In this case, compounds of general formula VI are reacted according to standard methods.

The carbon ester group of the compounds of general formula VI can be converted by reducing agents, for example lithium aluminum hydride, into the hydroxy methyl group. It in turn can be reacted with a halogenating agent, for example, thionyl chloride, to the halomethyl compound, for example to the chloromethyl derivative. The halogen substituent of the halomethyl group can be exchanged by nucleophilic substitution, for example, by reaction with sodium cyanide or with sodium methylate or with ammonia or ethylamine. The corresponding cyano, ethoxy, amino or ethylaminomethyl derivatives are obtained.

The carbon ester group of the compounds of general formula VI can be converted, under hydrolytic conditions, for example, by reaction with aqueous acid, into the free carboxylic acid or under aminolytic conditions, for example with ammonia solution, into the carboxylic acid amide. But it is also possible to convert the carbon ester group under conditions of a transesterification reaction with alcohols in the presence of an acid, for example 4-toluenesulfonic acid, into other esters. In the same way it is possible to obtain carboxylic acid esters by the reaction sequence of carboxylic acid and carboxylic acid halide. The carboxylic acid halides obtainable as intermediate products can be used for the production of carboxylic acid amides. For example, a carboxylic acid chloride can be reacted with ammonia or amines to carboxylic acid amide or substituted carboxylic acid amide.

The hydroxy methyl derivatives already described can be reacted by oxidizing agents, for example manganese dioxide, into the formyl derivatives, which in turn are initial materials of the derivatized formyl derivatives.

Moreover, the formyl derivatives can also be produced from the cyano derivatives of formula I by reduction. Complex metal hydrides, for example, sodium or lithium triethoxyaluminum hydride or aluminum nickel alloys in acids, preferably formic acid, are suitable as reducing agents.

By reduction of formyl derivatives with, for example, compounds containing amino groups, the imines or substituted imines can be obtained. In the same way it is possible to convert the formyl derivatives with semicarbazide or derivatives of semicarbazide into the semicarbazones or substituted semicarbazones, for example, thiosemicarbazones.

The formyl derivatives can also be used to achieve compounds which have a substituted hydrocarbon radical with more than one carbon atom as radical $R_2$. By reaction with Wittig reagents, a series of derivatives, for example, substituted cinnamic acid derivatives, can be obtained. The double bond in the reaction product of the Wittig reaction can be hydrogenated if required; thus, for example, the substituted phenylpropionic acid derivatives can be obtained.

The formyl derivatives can further be converted with metalorganic reagents, for example, Grignard reagents, into the corresponding secondary alcohols. The secondary alcohols can be converted, with oxidizing agents, for example, manganese dioxide, into the optionally substituted alkanoyl or benzoyl derivatives.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding application German P 38 11 574.3, filed Mar. 31, 1988, are hereby incorporated by reference.

EXAMPLES

EXAMPLE 1

4-[1-(1-Imidazolyl)-butyl]-benzoic acid methyl ester 6 g of 4-formylbenzoic acid is dissolved in 100 ml of tetrahydrofuran and mixed with 100 ml of a 1-molar solution of propyl magnesium bromide in tetrahydrofuran. After 6 hours of reaction time at room temperature the mixture is stirred into 100 ml of 2M of hydrochloric acid, extracted with ether and the ether phase is concentrated by evaporation. The crystalline material is filtered off with toluene on a suction filter and dissolved in 45 ml of dioxane and 5 ml of water and treated with 1.5 g of sodium boron hydride. After 15 minutes at room temperature, the mixture is added to 1M of hydrochloric acid, extracted with ethyl acetate, dried, concentrated by evaporation and chromatographed on 120 g of silica gel [toluene/acetic acid/water (10:10:1); upper phase after addition of a little water)]. 4.04 g of 4-(1-hydroxybutyl)-benzoic acid with a melting point of 109°–113° C. is obtained.

500 mg of it is stirred with 2.5 of thionyl chloride for 2.5 hours at room temperature. After distilling off the thionyl chloride, 2 ml of methanol and 1 ml of pyridine are added, stirred for 20 hours at room temperature and then the mixture is dispersed in 10 ml of 1M hydrochloric acid + 10 ml of ether. The ether phase is dried and concentrated by evaporation, the oily residue of 4-(1-chlorobutyl)-benzoic acid methyl ester is dissolved in 2 ml of dimethylformamide and added to a solution prepared from 270 mg of imidazole and 120 mg of 80% sodium hydride-oil suspension in 3 ml of dimethylformamide. After stirring for 20 hours at room temperature, it is added to excess 1M hydrochloric acid and extracted with ether. The water phase is alkalized with solid potassium carbonate and extracted with ethyl acetate. After drying and concentration by evaporation of the solvent, it is distilled on a bulb tube at 210°–230° C/0.03 mbar. 264 mg of 4-[1-(1-imidazolyl)-butyl]benzoic acid methyl ester is obtained.

EXAMPLE 2 a) 4-[1-(1-Imidazolyl)-butyl]-benzoic acid 23 g of the ester of example 1 is refluxed in 200 ml of concentrated hydrochloric acid for 20 hours. After concentration by evaporation in a vacuum, the residue is dissolved in water and brought to pH 8 with 50% sodium hydroxide solution. Then it is adjusted to pH 5–6 with 1M hydrochloric acid and evaporated to dryness. The crystalline residue is boiled several times with ethyl acetate and filtered. After concentration by evaporation, 20 g of 4-[1-(1-imidazolyl)-butyl]-benzoic acid with a melting point of 171°–172° C. is obtained.

4-[1-(1-Imidazolyl)-butyl]-benzoic acid, hydrochloride 1.0 g of 4-[1-(1-imidazolyl)-butyl]-benzoic acid is dissolved in 20 ml of ethanol and mixed with 10 ml of concentrated hydrochloric acid. The reaction mixture is precipitated into 100 ml of water and the precipitate is suctioned off. After recrystallization from ethanol, 0.95 g of 4-[1-(1-imidazolyl)-butyl]-benzoic acid, hydrochloride with a melting point of 38° C. is obtained.

EXAMPLE 3

4-[1-(1-Imidazolyl)-butyl]-benzamide 5 g of the acid from example 2 is stirred with 20 ml of thionyl chloride for 3 hours at room temperature. After concentration by evaporation of the excess thionyl chloride, the hydrochloride of the acid chloride is obtained as viscous oil.

2.5 g of acid chloride is dissolved in 20 ml of methylene chloride. Ammonia is introduced for 10 minutes, centrifuging is performed, the clear excess is concentrated by evaporation and chromatographed on silica gel. With methylene chloride/methanol (97:3), 170 mg of 4-[1-(1-imidazolyl)-butyl]-benzamide with a melting point of 132° C. is obtained.

EXAMPLE 4

4-[1-(1-Imidazolyl)-butyl]-benzonitrile a) 4.9 g of the amide of example 3 is dissolved in 50 ml of dioxane and 3.23 ml of pyridine and mixed with 3.16 ml of trifluoroacetic acid anhydride under ice cooled at 5° C. internal temperature. After 20 hours of stirring at room temperature it is added to half-saturated potassium carbonate solution, extracted with ether and the ether phase is dried and concentrated by evaporation. After distillation on a bulb tube at 200°–215° C./0.05 mbar, 3.2 g of 4-[1-(1-imidazolyl)-butyl]-benzonitrile is obtained, which, after crystallization from ether, melts at 63°–71° C.

b) By reaction of 4-bromobenzaldehyde with propyl magnesium bromide under standard conditions, 1-(4-bromophenyl)-1-butanol with a boiling point of 180° C./0.03 mbar is obtained.

380 g of 1-(4-bromophenyl)-1-butanol is put in a flask and mixed at −30° C. with 240 ml of thionyl chloride and stirred for one hour more at room temperature. The mixture is allowed to stand overnight. The reaction mixture is stirred into 10 l of water and then extracted with ether. The ether phases are dried and concentrated by evaporation in a vacuum. 123 g of imidazole is put in a second flask and dissolved in 1500 ml of dimethylformamide. 58 g of sodium hydride is now slowly added under nitrogen. It is stirred for 2 more hours at room temperature and the resulting chlorine compound is slowly instilled. The reaction mixture is allowed to stand overnight. Then the reaction mixture is precipitated into 10 l of water, extracted 3 times with 1 l of ether each time and the organic phase is rewashed with a total of 5 l of water. Then the remaining solvent is removed in a vacuum and the remaining residue is fractionally distilled. 300 g of 1-[1-(4-bromophenyl)-butyl]-imidazole with a boiling point of 200° C./0.025 mbar is obtained.

2.79 g of 1-[1-(4-bromophenyl)-butyl]-imidazole and 1.8 g of copper(I) cyanide are heated in 5 ml of N-methylpyrrolidine for 4 hours at 180° C. under a protecting gas atmosphere (argon). After cooling, it is precipitated in 50 ml of ammonia solution, stirred for 15 more minutes at room temperature and extracted with ethyl acetate. After concentration by evaporation in a vacuum 1.95 g of dark oil is obtained. This oil is distilled on a bulb tube in a vacuum; boiling point 200°–215° C./0.05 mbar. The resulting distillate is recrystallized from ethanol/petroleum ether. 1.54 g of 4-[1-(1-imidazolyl)-butyl]-benzonitrile with a melting point of 63°–71° C. is obtained.

EXAMPLE 5

4-[1-(1-Imidazolyl)-butyl]-benzyl alcohol 1.0 g of benzoic acid methyl ester of example 1 is dissolved in 15 ml of tetrahydrofuran and mixed with 0.15 g (3.9 mmol) of lithium aluminum hydride and left at room temperature for 1 hour. The reaction solution is mixed with 50% sodium hydroxide solution and the organic phase is decanted. The organic phase is concentrated by evaporation in a vacuum and distilled on a bulb tube, boiling point 200° C./0.03 mbar. 0.6 g of 4-[1-(1-imidazolyl)-butyl]-benzyl alcohol is obtained.

EXAMPLE 6

4-[1-(1-Imidazolyl)-butyl]-benzaldehyde a) 0.1 g of the substituted benzyl alcohol of example 5 is dissolved in 10 ml of methylene chloride, mixed with 0.15 g of manganese dioxide and refluxed for 6 hours. After cooling, the reaction mixture is filtered on silica gel and concentrated by evaporation in a vacuum. The residue is distilled on a bulb tube, boiling point 200° C./0.03 mbar. 0.08 g of 4-[1-(1-imidazolyl)-butyl]-benzaldehyde is obtained.

b) 10 g of nitrile of example 4 is refluxed with 10 g of aluminum nickel alloy in 150 ml of formic acid/water (75:25) for 1 hour. It is filtered on kieselguhr, the filtrate is alkalized with solid potassium carbonate, 100 ml of aqueous ammonia is added and extracted with ether. After drying and concentration by evaporation of the ether, it is distilled on a bulb tube; 9.1 g of 4-[1-(1-imidazolyl)butyl]-benzaldehyde is obtained, melting 200° C./0.03 mbar.

EXAMPLE 7

1-[4-[1-(1-Imidazolyl)-butyl]-phenyl]-ethanol 460 mg of the aldehyde of example 5 in 8 ml of ether is mixed with 1.5 ml of a 3M methyl magnesium bromide solution in ether with ice cooling and is stirred for 20 hours at room temperature; 10 ml of tetrahydrofuran is added and heated to 60° C. in 6 hours. It is added to 1M of hydrochloric acid, extracted with ether, then the water phase is alkalized with potassium carbonate and extracted with ether. After drying and concentration by evaporation of this ether phase, the residue is chromatographed on silica gel (methylene chloride/methanol (95:5)). 300 mg of the title compound is obtained.

EXAMPLE 8

4'-[1-(1-Imidazolyl)-butyl]-acetophenone 200 mg of the alcohol of example 7 is stirred in 10 ml of methylene chloride with 1 g of manganese dioxide overnight. It is suctioned off, concentrated by evaporation and the residue is distilled at 180° C./0.03 hPa. 100 mg of the title compound is obtained as colorless oil.

EXAMPLE 9

1-[4-[1-(1-Imidazolyl)-butyl]-phenyl]-2-methyl-1-propanol

Analogously to example 7 with the use of 2-propyl magnesium bromide.

EXAMPLE 10

[4-[1-(1-Imidazolyl)-butyl]-phenyl]-2-propylketone

Analogously to example 8 of the compound of example 9; boiling point 250° C./0.04 mbar.

EXAMPLE 11

4'-[1-(1-Imidazolyl)-butyl]-propiophenone

The 4-[1-(1-imidazolyl)-butyl]-benzonitrile obtained according to example 4 is reacted under standard conditions with ethyl magnesium bromide. 0.65 g of 4-[1-(1-imidazolyl)-butyl]-propiophenone with a boiling point of 235° C./0.03 mobile is obtained.

The compounds of examples 12–16 are obtained by reaction of 4-[1-(1-imidazolyl)-butyl]-benzonitrile with the corresponding Grignard compounds analogously to example 11.

EXAMPLE 12

[4-[1-(1-Imidazolyl)-butyl]-phenyl]-propylketone

Boiling point 200° C./0.03 mbar.

EXAMPLE 13

4-[i-(1-Imidazolyl)-butyl]-phenyl]-butylketone

Boiling point 200° C./0.03 mbar.

EXAMPLE 14

[4-[1-(1-Imidazolyl)-butyl]-phenyl]-pentylketone

Boiling point 210° C./0.04 mbar.

EXAMPLE 15

[4-[1-(1-Imidazolyl)-butyl]-phenyl]-hexylketone

Boiling point 250° C./0.03 mbar.

EXAMPLE 16

Cyclohexyl-[4-[1-(1-imidazolyl)-butyl]-phenyl]-ketone

Boiling point 250° C./0.04 mbar.

EXAMPLE 17

4-[1-(1-Imidazolyl)-butyl]-benzophenone

The 4-[1-(1-imidazolyl)-butyl]-benzonitrile is reacted with phenylmagnesium bromide under standard conditions analogously to example 11 in tetrahydrofuran. 0.83 g of 4-[1-(1-imidazolyl)-butyl]-benzophenone with a boiling point of 175° C./0.03 mbar is obtained.

EXAMPLE 18

4'-[Cyclohexyl-(1-imidazolyl)-methyl]-acetophenone

A Grignard solution is produced from 10 g of 4'-bromoacetophenone dimethylketal and 2 g of magnesium in 100 ml of ether with use of 1,2-dibromomethane. A solution of 4 g of cyclohexanealdehyde in 20 ml of ether is instilled in it. After 20 hours at room temperature, 100 ml of 1M hydrochloric acid is added and stirred vigorously for 1 hour. The ether phase is separated, dried, concentrated by evaporation and the residue is chromatographed on silica gel with toluene/ethyl acetate (gradient 0–20% ethyl acetate). 5 g of (4acetylphenyl)-cyclohexylmethanol is obtained.

It is left with 10 ml of thionyl chloride for 1 hour at room temperature. The excess thionyl chloride is removed in a vacuum and the residue is reacted with 10 g of imidazole for 20 hours at 130° C. After chilling, it is poured on an excess of 2M hydrochloric acid, extracted with ether, the aqueous phase is alkalized with potassium carbonate and extracted with ethyl acetate. After drying and concentration by evaporation of the solvent, it is distilled on a bulb tube. 2 g of the title compound is obtained. Boiling point 230°–250° C./0.03 mbar.

EXAMPLE 19

4-[1-(1-Imidazolyl)-butyl]-benzoic acid dimethylamide 1.2 g of 4-[1-(1-imidazolyl)-butyl]-benzoic acid is dissolved in 10 ml of dimethylformamide, mixed at 0° C. with 1 ml of N-ethylmorpholine and 1 ml of chloroformic acid isobutyl ester. It is stirred for 30 minutes at 0° C., 2 ml of dimethylamino solution is instilled and stirred for 2 hours at 0° C. It is stirred into 500 ml of water, extracted with ethyl acetate and the organic phase is concentrated by evaporation in a vacuum. The remaining residue is distilled on a bulb tube. Boiling point: 260° C./0.03 mbar. 0.9 g of 4-[1-(1-imidazolyl)-butyl]-benzoic acid dimethylamide is obtained.

EXAMPLE 20

4-[1-(1-Imidazolyl)-butyl]-benzoic acid pyrrolidide 5.0 g of 4-[1-(1-imidazolyl)-butyl]-benzoic acid (of example 2) is stirred for 2 hours with 50 ml of thionyl chloride at room temperature. Then 100 ml of toluene is added and the solution is concentrated by evaporation in a vacuum. It is dissolved in 40 ml of methylene chloride, mixed with 5 ml of pyrrolidine and stirred for 3 hours at room temperature. 50 ml of water is added to it and extracted with ethyl acetate. It is again concentrated by evaporation in a vacuum and the residue is distilled on a bulb tube; boiling point 260° C./0.02 mbar. 4-[1-(1-imidazolyl)-butyl]-benzoic acid pyrrolidide is obtained.

Analogously to example 20, the compounds of examples 21–30 are obtained by reactions of 4-[1-(1-imidazolyl)-butyl]-benzoic acid on the acid chloride with the corresponding amines.

EXAMPLE 21

N-butyl-4-[1-(1-imidazolyl)-butyl]-benzamide

Boiling point 250° C./0.04 mbar.

EXAMPLE 22

N-cyclohexyl-4-[1-(1-imidazolyl)-butyl]-benzamide

Boiling point 250° C./0.03 mbar.

EXAMPLE 23

4-[1-(1-imidazolyl)-butyl]-benzanilide

Melting point 173°–175° C.

EXAMPLE 24

N-(4'-tolyl)-4-[1-(1-imidazolyl)-butyl]-benzamide

Melting point 155°–157° C.

EXAMPLE 25

N-(4-chlorophenyl)-4-[1-(1-imidazolyl)-butyl]-benzamide

Melting point 152° C.

EXAMPLE 26

N-benzyl-4-[1-(1-imidazolyl)-butyl]-benzamide

Melting point 137°–140° C.

EXAMPLE 27

N-(3-pyridyl)-4-[1-(1-imidazolyl]-butyl]-benzamide

EXAMPLE 28

4-[1-(1-Imidazolyl)-butyl]-benzoic acid-(4-methylpiperidide)

Boiling point 250° C./0.03 mbar.

EXAMPLE 29

4-[1-(1-Imidazolyl)-butyl]-N-methyl-N-phenyl-benzamide

EXAMPLE 30

4-[1-(1-Imidazolyl)-butyl]-benzoic acid (N'-methylpiperazide)

Boiling point 200° C./0.030 mbar.

EXAMPLE 31

4-[1-(1-Imidazolyl)-butyl]-benzoic acid methyl ester 1.0 of 4-[1-(1-imidazolyl)-butyl]-benzoic acid, hydrochloride (of example 2) is dissolved in 30 ml of methanol, hydrochloric-acid gas is introduced for 10 minutes, refluxed for 30 minutes and concentrated by evaporation. The residue is distilled on a bulb tube, boiling point 190° C./0.03 mbar. 0.55 g of 4-[1-(1-imidazolyl)-butyl]-benzoic acid methyl ester is obtained.

EXAMPLE 32

4-[1-(1-Imidazolyl)-butyl]-benzoic acid butyl ester

Analogously to example 31, the 4-[1-(1-imidazolyl)-butyl]-benzoic acid butyl ester with a boiling point of 190° C./0.03 is obtained by reaction of the substituted benzoic acid with butanol.

EXAMPLE 33

4-[1-(1-Imidazolyl)-butyl]-benzoic acid isopropyl ester

Boiling point 200° C./0.03 mbar.

EXAMPLE 34

4-[1-(1-Imidazolyl)-butyl]-benzoic acid-(1-methylbutyl) ester

Boiling point 200° C./0.03 mbar, analogously to example 31.

EXAMPLE 35

4-[1-(1-Imidazolyl)-butyl]-benzoic acid cyclohexyl ester 1 g of 4-[1-(1-imidazolyl)-butyl]-benzoic acid is converted, analogously to example 20, into the acid chloride; it is dissolved in 10 ml of methylene chloride, mixed with 360 mg of cyclohexanol and 3 ml of pyridine, after 20 hours at room temperature it is added to excess 1M hydrochloric acid and extracted with ether. The water phase is alkalized with potassium carbonate and extracted with ethyl acetate. After drying and concentration by evaporation, the residue is distilled on a bulb tube. 915 mg of the title compound is obtained as oil with a boiling point of 200° C./0.03 mbar.

Analogously to example 35, the compounds of examples 36–38 are obtained by reaction of 4-[1-(1-imidazolyl)-butyl]-benzoic acid on the acid chloride with the corresponding alcohols.

EXAMPLE 36

4-[1-(1-Imidazolyl)-butyl]-benzoic acid-(2-methoxyethyl) ester

Boiling point 250° C./0.03 mbar.

EXAMPLE 37

4-[1-(1-Imidazolyl)-butyl]-benzoic acid-(2methylmercaptoethyl) ester

Boiling point 200° C./0.03 mbar.

EXAMPLE 38

4-[1-(1-Imidazolyl)-butyl]-benzoic acid-(2dimethylaminoethyl) ester

Boiling point 220° C./0.03 mbar.

EXAMPLE 39

4-[1-(1-Imidazolyl)-butyl]-benzoic acid tert-butyl ester 1 g of 4-[1-(1-imidazolyl)-butyl]-benzoic acid with 3.4 g of N,N-dimethylformamide-di-tert-butylacetal in 6 ml of toluene is warmed to 100° C. for 1 hour. It is then dispersed in ether/1M hydrochloric acid, the water phase is alkalized with potassium carbonate and extracted with ethyl acetate; after concentrated by evaporation of the solvent, it is distilled on a bulb tube. 0.58 g of the title compound is obtained, boiling point 200° C./0.03 mbar.

EXAMPLE 40

1-[4-[1-1-Imidazolyl)-butyl]-phenyl]-1-propanol 0.45 g of 4-[1-(1-imidazolyl)-butyl]-propiophenone of example 1 is dissolved in 10 ml of dioxane and mixed with 0.130 g of sodium boron hydride and stirred overnight at room temperature. The batch is then precipitated in 100 ml of water and extracted with ether. The solvent is concentrated by evaporation in a vacuum and the remaining residue is distilled at 220° C./0.03 mbar on a bulb tube. 0.250 g of 1-[4-[1–1-imidazolyl)-butyl]-phenyl]-1-propanol is obtained.

EXAMPLE 41

3'-[1-(1-Imidazolyl)-butyl]-trans-cinnamic acid ethyl ester a) 1-[1-(3-Bromophenyl)-butyl]-imidazole 3-Bromobenzaldehyde is reacted with propyl magnesium bromide to 1-(3-bromophenyl)-butanol under standard conditions.

4.0 g (17.5 mmol) of 1-(3-bromophenyl)-butanol is stirred with 4 ml of thionyl chloride for 1 hour at room temperature. 10 ml of toluene is added to the reaction mixture. 1-Chloro-1-(3-bromophenyl)-butanol is obtained after concentration by evaporation in a vacuum. 1.3 g of imidazole is dissolved in 20 ml of dimethylformamide and mixed with 0.6 g of sodium hydride (80% in oil) under argon protective gas atmosphere. It is stirred for 1 hour at room temperature. The chlorine compound is instilled into 15 ml of dimethylformamide and allowed to stand overnight. The mixture is precipitated in 200 ml of water and extracted with ethyl acetate. The organic phase is concentrated by evaporation in a vacuum and then distilled on a bulb tube at 150° C./0.03 mbar. 1.6 g of 1-[1-(3-bromophenyl)-butyl]-imidazole is obtained as a viscous oil.

b) 11.0 g of the compound of a), 8.8 ml of acrylic acid ethyl ester, 20 ml of tributylamine, 1.86 g of triphenylphosphine and 0.82 g of palladium(II) acetate are added together and stirred for 18 hours at 100° C. (J. Amer. Chem. Soc. 96, 1133 (1974)). The reaction mixture is precipitated in 200 ml of 1 n hydrochloric acid. It is extracted three times with ether and the extract is discarded. The aqueous solution is made alkaline with 50% sodium hydroxide solution and again extracted with ether. The organic phases are combined, dried and concentrated by evaporation. The remaining residue is distilled on a bulb tube, boiling point 230° C./0.03 mbar. 7.63 g of 3'-[1-(1-imidazolyl)-butyl)-trans-cinnamic acid ethyl ester (b) is obtained.

EXAMPLE 42

3'-[1-(1-Imidazolyl)-butyl]-trans-cinnamic acid 7.6 g of 3'-[1-(1-imidazolyl)-butyl]-transcinnamic acid ethyl ester (of example 41) is dissolved in 100 ml of ethanol and mixed with 50 ml of 10% sodium hydroxide solution. The reaction mixture is allowed to stand for 2 hours at 100° C. It is evaporated to dryness, the residue is made acid with concentrated hydrochloric acid, the precipitated salt is suctioned off and rinsed with ethanol. 5.26 g (67% of th.) of 3'[1-(1-imidazolyl)-butyl]-trans-cinnamic acid is obtained.

EXAMPLE 43

3-[3-[1-(1-Imidazolyl)-butyl]-phenyl]-propionic acid 1.08 g of 3-[1-(1-imidazolyl)-butyl]-cinnamic acid (example 42) is dissolved in 20 ml of methanol and mixed with 100 mg of palladium on carbon (10%) and hydrogenated at normal pressure. After 2 hours, the reaction mixture does not take up any more hydrogen. Then the catalyst is filtered off on kieselguhr and the filtrate is concentrated by evaporation in a vacuum. 1.05 g of 3-[3-[1-(1-imidazolyl)-butyl]-phenyl]propionic acid is obtained

EXAMPLE 44

4-[1-(1-Imidazolyl)-butyl]-benzyl chloride, hydrochloride

4-[1-(1-Imidazolyl)-butyl]-benzyl chloride, hydrochloride is obtained by reaction of the corresponding substituted benzyl alcohol of example 5 with thionyl chloride under standard conditions.

EXAMPLE 45

1-[1-(4-Methoxymethylphenyl)-butyl]-imidazole 0.4 g of the substituted benzyl chloride of example 44 is dissolved in 10 ml of methanol and is mixed by instillation with a methanolic solution, prepared from 20 ml of methanol and 0.42 g of sodium hydride. It is stirred overnight at room temperature. Then the methanol is removed in a vacuum, the residue is mixed with 50 ml of water and extracted with ether. The organic phase is dried and concentrated by evaporation. It is distilled on a bulb tube, boiling point 250° C./0.03 mbar. 0.19 g of 1-[1-(4-methoxy-methylphenyl)-butyl]imidazole is obtained.

EXAMPLE 46

1-[1-(4-Butoxymethylphenyl)-butyl]-imidazole

Analogously to example 45, 1-[1-(4-butoxymethylphenyl)-butyl]-imidazole is obtained by reaction of the substituted benzyl chloride with sodium butylate. Boiling point 250° C./0.03 mbar.

EXAMPLE 47

1-[1-(4-Phenoxymethylphenyl)-butyl]-imidazole

Boiling point 250° C./0.03 mbar.

Analogously to example 45, 1-[1-(4-phenoxymethylphenyl)-butyl]-imidazole is obtained by reaction of the substituted benzyl chloride with sodium phenolate.

EXAMPLE 48

4-[1-(1-Imidazolyl)-butyl]-phenyl acetonitrile 0.545 g of the benzyl chloride obtained in example 44 is dissolved in 10 ml of dimethyl sulfoxide and mixed with 0.125 g of sodium cyanide and stirred overnight at room temperature. The reaction mixture is precipitated in 200 ml of water and extracted with ethyl acetate. The organic phase is concentrated to dryness in a vacuum and the residue is distilled on a bulb tube, boiling point 250° C./0.03 mbar. 0.4 g of 4-[1-(1-imidazolyl)butyl]-phenyl acetonitrile is obtained.

EXAMPLE 49

1-[4-[1-(1-Imidazolyl)-butyl]-benzyl]-pyrrolidine 0.15 g of the substituted benzoic acid pyrrolidide (example 20) is dissolved in 3 ml of tetrahydrofuran and instilled in a suspension consisting of 0.2 g of lithium aluminum hydride in 5 ml of tetrahydrofuran. It is refluxed for 2 hours. The reaction solution is mixed in 50% sodium hydroxide solution and the organic phase is decanted and evaporated to dryness. The residue is distilled on a bulb tube, boiling point 201° C./0.03 mbar. 0.1 g of 1-[4-[1-(1-imidazolyl)-butyl]-benzyl]pyrrolidine is obtained.

EXAMPLE 50

1-[1-(4-Hydroxyiminomethylphenyl)-butyl]-imidazole 0.5 g of 4-[1-(1-imidazolyl)-butyl]-benzaldehyde (see example 6) is dissolved in 2 ml of pyridine and mixed with 0.215 g of hydroxylamine hydrochloride. It was stirred overnight at room temperature and precipitated in 30 ml of water and extracted with ether. After removal of the solvent under vacuum, 0.4 of 1-[1-(4-hydroxyiminomethylphenyl)-butyl]-imidazole is obtained as yellow oil.

EXAMPLE 51

1-[1-(4-Methoxyiminomethylphenyl)-butyl]-imidazole 0.5 g of 4-[1-(1-imidazolyl)-butyl]-benzaldehyde (of example 6) is dissolved with 0.42 g of O- methylhydroxylamine hydrochloride in 20 ml of pyridine and stirred overnight. It is poured into 100 ml of water and extracted with ethyl acetate. The organic phase is concentrated by evaporation in a vacuum and distilled on a bulb tube, boiling point 200° C./0.03 mbar. 0.39 g of 1-[1-(4-methoxyiminomethylphenyl)-butyl]imidazole is obtained.

Analogously to example 50 and 51, the compounds of examples 52–56 are obtained by reactions of 4-[1-(1-imidazolyl)-butyl]-benzaldehyde with the corresponding amines.

EXAMPLE 52

1-[1-(4-Ethoxyiminomethyl-phenyl)-butyl]-imidazole

EXAMPLE 53

1-[1-(4-Allyloxyiminomethyl-phenyl)-butyl]-imidazole

EXAMPLE 54

1-[1-(4-Benzyloxyiminomethyl-phenyl)-butyl]-imidazole

EXAMPLE 55

1-[1-[4-(4-Nitrobenzyloxyimino)-methyl-phenyl]-butyl]imidazole

EXAMPLE 56

1-[1-[4-(2,3,4,5,6-pentafluorobenzyloxyimino)-methylphenyl]-butyl]-imidazole

EXAMPLE 57 alpha-[4-[1-(1-Imidazolyl)-butyl]-phenyl]-benzyl alcohol

By reduction of the ketone of example 17 with sodium boron hydride in dioxane/water (90:10); boiling point 250° C./0.03 mbar.

EXAMPLE 58

1-[1-(4-Semicarbazonomethylphenyl)-butyl]-imidazole 0.5 g of 4-[1-(1-imidazolyl)-butyl]-benzaldehyde (example 6) is dissolved in 20 ml of pyridine and mixed with 1.37 g of semicarbazine hydrochloride. It is stirred overnight at room temperature, then the reaction mixture is precipitated in 100 ml of water and extracted with methylene chloride. The organic solution is concentrated by evaporation in a vacuum. 0.42 mg of the title compound with a melting point of 38° C. is obtained.

EXAMPLE 59

4-[1-(1-Imidazolyl)-butyl]-trans-cinnamic acid ethyl ester 0.228 g of 4-[1-(1-imidazolyl)-butyl]-benzaldehyde (example 6) is dissolved in 5 ml of dioxane and mixed with 0.35 g of carbethoxymethylene triphenyl phosphorane and stirred for 48 hours at room temperature. The reaction mixture is poured into 100 ml of water and extracted with ethyl acetate. The organic phases are combined and evaporated to dryness, the residue is distilled on a bulb tube. 0.15 g of the title compound with a boiling point of 200°-220° C./0.03 mbar is obtained.

EXAMPLE 60

4-[1-(1-Imidazolyl)-butyl]-trans-cinnamic acid, hydrochloride

The title compound is obtained by saponification of the ethyl ester of example 59 and then conversion into the hydrochloride.

EXAMPLE 61

3-[1-(1-imidazolyl)-butyl]-propionic acid ethyl ester

The title compound is obtained by esterification of the acid of example 43 with ethanol under standard conditions.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An imidazole of the formula

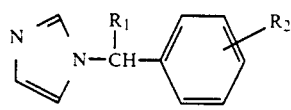

in which

R$_1$ is a saturated or unsaturated, straight-chain or branched-chain hydrocarbon radical having 1 to 10 carbon atoms, a cycloalkyl radical having 3 to 9 carbon atoms, a cycloalkylalkyl radical having 4 to 12 carbon atoms or an arylalkyl radical with 7 to 10 carbon atoms; and R$_2$ is a formyl group or an amine-containing derivative of a formyl group, said derivative resulting from the reaction of a formyl group with hydroxylamine, O-methylhydroxylamine, O-ethylhydroxylamine, O-allylhydroxylamine, O-benzylhydroxylamine, O-4-nitrobenzyloxyhydroxylamine, O-2,3,4,5,6-pentafluorobenzyloxyhydroxylamine, semicarbazide, thiosemicarbazide, ethylamine or aniline, an alkanoyl group with 2 to 10 carbon atoms, an alkanoyl group having 2 to 10 carbon atoms which is substituted with halogen, C$_{1-4}$-alkoxy, amino, hydroxyl, and/or cyano, a benzoyl group, or a benzoyl group which is substituted with halogen, C$_{1-4}$-alkyl, methoxy, amino, hydroxyl, and/or cyano;

or a pharmaceutically acceptable salt thereof.

2. A compound which is 4-(1-(1-imidazolyl)-butyl)-benzaldehyde;
4'-(1-(1-imidazolyl)-butyl)-propiophenone;
4-(1-(1-imidazolyl)-butyl)-benzanilide;
4-(1-(1-imidazolyl)-butyl)-benzophenone;
4-[1-(1-imidazolyl)-butyl]-benzamide;
4'-[1-(1-imidazolyl)-butyl]-acetophenone;
[4-[1-(1-imidazolyl)-butyl]-phenyl]-2-propyl-ketone;
[4-[1-(1-imidazolyl)-butyl-9 -phenyl]-propylketone;
[4-[1-(1-imidazolyl)-butyl]-phenyl]-butylketone;
[4-[1-(1-imidazolyl)-butyl]-phenyl]-pentylketone;
[4-[1-(1-imidazolyl)-butyl]-phenyl]-hexylketone;
cyclohexyl-[4-[1-(1-imidazolyl)-butyl]-phenyl]ketone;
4'-[cyclohexyl-(1-imidazolyl)-methyl]-acetophenone;
N-butyl-4-[1-(1-imidazolyl)-butyl]-benzamide;
N-cyclohexyl-4-[1-(1-imidazolyl)-butyl]-benzamide;
N-p-tolyl-4-[1-(1-imidazolyl)-butyl]-benzamide;
N-(4-chlorophenyl)-4-[1-(1-imidazolyl)-butyl]-benzamide;
N-benzyl-4-[1-(1-imidazolyl)-butyl]-benzamide; or
4-[1-(1-imidazolyl)-butyl]-N-methyl-N-phenyl-benzamide.

3. A pharmaceutical composition comprising a compound of claim 1 in a pharmaceutically acceptable carrier.

4. A pharmaceutical composition comprising a compound of claim 2 in a pharmaceutically acceptable carrier.

5. A compound of claim 1, wherein $R_2$ is a carboxylic acid ester or a carboxylic acid amine.

6. A method of treating estrogen-stimulated tumors in a patient in need of such treatment, comprising administering an effective amount of a compound of claim 1.

7. A method according to claim 6, wherein the effective amount is 0.0001–10 mg/kg/day.

8. A method of ameliorating male infertility in a host comprising administering an effective amount of a compound of claim 1.

9. A method according to claim 8, wherein the effective amount is 0.0001–10 mg/kg/day.

10. A method of inhibiting ovulation comprising administering to a female otherwise capable of ovulation an effective amount of a compound of claim 1.

11. A method according to claim 10, wherein the effective amount is 0.0001–10 mg/kg/day.

12. A method of treating imminent myocardial infarction in a patient in need of such treatment comprising administering an effective amount of a compound of claim 1.

13. A method according to claim 12, wherein the effective amount is 0.0001–10 mg/kg/day.

14. A method of treating estrogen-stimulated tumors, ameliorating male infertility, inhibiting ovulation and/or treating imminent myocardial infarction comprising administering to a patient in need of such treatment an effective amount of a compound of claim 2.

15. An imidazole according to claim 1, wherein $R_1$ is methyl, ethyl, propyl, propenyl, isopropyl, butyl, hexyl, octyl, decyl, cyclopentyl, cyclohexyl, cyclopentylmethyl, cyclohexylmethyl or benzyl.

16. An imidazole according to claim 1, wherein $R_1$ is a propyl radical.

17. An imidazole according to claim 1, wherein $R_1$ is acetyl, propionoyl, butyryl, valeryl, or caproyl, in each case being unsubstituted or substituted by halogen, $C_{1-4}$-alkoxy, amino, hydroxyl and/or cyano; unsubstituted benzoyl; or benzoyl substituted by halogen, $C_{1-4}$alkyl, methoxy, amino, hydroxyl, and/or cyano.

* * * * *

UNITED STATES PATENT AND TRADEMARK OFFICE
CERTIFICATE OF CORRECTION

PATENT NO. : 5,045,558

DATED : Sept. 3, 1991

INVENTOR(S) : STREHLKE et al.

It is certified that error appears in the above-identified patent and that said Letters Patent is hereby corrected as shown below:

COLUMN 18;

CLAIM 2; LINE 9:

Please change 9 to a bracket, "]".

Signed and Sealed this

Twelfth Day of January, 1993

*Attest:*

DOUGLAS B. COMER

*Attesting Officer*   Acting Commissioner of Patents and Trademarks